US006508838B2

(12) United States Patent
Lee et al.

(10) Patent No.: US 6,508,838 B2
(45) Date of Patent: *Jan. 21, 2003

(54) COMPOSITIONS FOR MEDICAL IMPLANTATION

(75) Inventors: Minako Yoshioka Lee, Seattle, WA (US); David Rodney Eyre, Seattle, WA (US); Mary Ann Eklof Weis, Everett, WA (US)

(73) Assignee: Washington Research Foundation, Seattle, WA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/785,614

(22) Filed: Feb. 16, 2001

(65) Prior Publication Data

US 2001/0016203 A1 Aug. 23, 2001

Related U.S. Application Data

(63) Continuation of application No. 09/063,958, filed on Apr. 21, 1998, now Pat. No. 6,190,412.
(60) Provisional application No. 60/044,033, filed on Apr. 22, 1997.

(51) Int. Cl.$^7$ .................................................. A61F 2/62
(52) U.S. Cl. ............................... 623/11.11; 623/23.76; 623/23.57
(58) Field of Search ........................ 623/11.11, 16.11, 623/23.57, 23.76; 424/56, 54; 453/228.1

(56) References Cited

U.S. PATENT DOCUMENTS

| 5,073,114 A | 12/1991 | Detsch |
| 5,162,430 A | 11/1992 | Rhee et al. |
| 5,226,914 A | 7/1993 | Caplan et al. |
| 5,258,029 A | 11/1993 | Chu et al. |
| 5,258,367 A | 11/1993 | Bazer et al. |
| 5,591,453 A | 1/1997 | Ducheyne et al. |
| 5,654,173 A | 8/1997 | Jacobs et al. |
| 5,824,087 A | 10/1998 | Aspden et al. |
| 5,854,207 A | 12/1998 | Lee et al. |
| 5,876,446 A | 3/1999 | Agrawal et al. |
| 5,879,663 A * | 3/1999 | Nakabayashi et al. ......... 106/35 |
| 6,190,412 B1 * | 2/2001 | Lee et al. ................. 623/11.11 |

FOREIGN PATENT DOCUMENTS

| WO | WO 93/00935 | 1/1993 |
| WO | WO 93/07271 | 4/1993 |

OTHER PUBLICATIONS

Ling, P., and Roberts, R.M., "Uteroferrin and Intracellular Tartrate–resistant Acid Phosphatases Are the Products of the Same Gene," *J. Biol. Chem.* 268:6896–6902, 1993.

Hayman, A.R., and Cox, T.M., "Purple Acid Phosphatase of the Human Macrophage and Osteoclast," *J. Biol. Chem.* 269:1294–1300, 1994.

Ketcham, C.M., et al., "Molecular Cloning of the Type 5, Iron–containing, Tartrate–resistant Acid Phosphatase from Human Placenta," *J. Biol. Chem.* 264:557–563, 1989.

Ek–Rylander, B., et al., "Cloning, Sequence, and Developmental Expression of a Type 5, Tartrate–resistant, Acid Phosphatase of Rate Bone," *J. Biol. Chem.* 266:24684–24689, 1991.

Ek–Rylander, B., et al., "Comparative studies of rat recombinant purple acid phosphatase and bone tartrate–resistant acid phosphatase," *Biochem. J.* 321:305–311, 1997.

(List continued on next page.)

*Primary Examiner*—David J. Isabella
(74) *Attorney, Agent, or Firm*—Christensen, O'Connor, Johnson, Kindness PLLC

(57) ABSTRACT

A composition or device suitable for orthopedic or dental implantation to bone, characterized by tartrate-resistant acid phosphatase (TRAP) adsorbed to a porous hydroxyapatite substratum.

8 Claims, 3 Drawing Sheets

OTHER PUBLICATIONS

Yam, L.T., et al., "Tartrate–Resistant Acid Phosphatase Isoenzyme in the Reticulum Cells of Leukemic Reticuloendotheliosis," *N. Engl. J. Med.* 284:357–360, 1971.

Lau, K.H., et al., "Characterization and Assay of Tartrate–Resistant Acid Phosphatase Activity in Serum: Potential Use to Assess Bone Resorption," *Clin. Chem.* 33:458–462, 1987.

Chamberlain, P., et al., "Generation and Characterization of Monoclonal Antibodies to Human Type–5 Tartrate–Resistant Acid Phosphatase: Development of a Specific Immunoassay of the Isoenzyme in Serum," *Clin. Chem.* 41:1495–1499, 1995.

Reinholt, F., et al., "Ultrastructural Localization of a Tartrate Resistant Acid ATPase in Bone," *J. Bone Miner. Res.* 5:1055–1061, 1990.

Zaidi, M., et al., "Inhibition of Osteoclastic Acid Phosphatase Abolishes Bone Resorption," *Biochem. Biophys. Res. Commun.* 159:68–71, 1989.

Hayman, A.R., et al., "Mice lacking tartrate–resistant acid phosphatase (Acp 5) have disrupted endochondral ossification and mild osteopetrosis," *Development* 122:3151–3162, 1996.

Suda, T., et al., "Modulation of Osteclast Differentiation," *Endocrine Reviews* 13:66–80, 1992.

Roodman, G.D., "Advances in bone biology: The osteoclast," *Endocrine Reviews* 17:308–332, 1996.

Suda, T., et al., "Modulation of Osteoclast Differentiation by Local Factors," *Bone* 17(2S):87S–91S, 1995.

Yasuda, H., et al., "Osteoclast differentiation factor is a ligand for osteoprotegerin/osteoclastogenesis–inhibitory factor and is identical to TRANCE/RANKL," *Proc. Natl. Acad. Sci. USA* 95:3597–3602, 1998.

Roach, H.I., "New Aspects of Endochrondral Ossification in the Chick: Chondrocyte Apoptosis, Bone Formation by Former Chondrocytes, and Acid Phosphatase Activity in the Endochondral Bone Matrix," *J. Bone Miner. Res.* 12:795–805, 1997.

Yamamoto, T. and Nagai, H., "A Histochemical Study of Acid Phosphatases in Medullary Bone Matrix and Osteoclasts in Laying Japanese Quail," *J. Bone Miner. Res.* 7:1267–1273, 1992.

Yamamoto, T. and Nagai, H., "Tartrate–resistant acid phosphatase accumulated in the matrix of developing medullary bone induced by estrogen treatment of male Japanese quail," *J. Bone Mier. Res.* 9:1153–1157 (Abstract), 1994.

Fukushima, O., Bekker, P.J. and Gay, C.V., "Ultrastructural Localization of Tartrate–Resistant Acid Phosphatase (Purple Acid Phosphatase) Activity in Chicken Cartilage and Bone," *Amer. J. Anat.* 191:228–236, 1991.

Allen et al., "Purification and Characterization of Human Bone Tartrate–Resistant Acid Phosphatase," *J. Bone Miner. Res.* 4:47–55, 1989.

Lee, M.Y., et al., "Identification and Characterization of Osteoclast Progenitors by Clonal Analysis of Hematopoietic Cells," *Blood* 80:1710–1716, 1992.

Lee, M.Y., and Baylink, D.J., "Hypercalcemia, Excessive Bone Resorption, and Neutrophilia in Mice Bearing a Mammary Carcinoma," *Proc. Soc. Exp. Biol. Med.* 172:424–429, 1983.

Muguruma, Y., and Lee, M.Y., "Isolation and Characterization of Murine Clonogenic Osteoclast Progenitors by Cell Surface Phenotype Analysis," *Blood* 91:1272–1279, 1998.

Lee, M.Y., et al., "Isolation of a murine osteoclast colony–stimulating factor," *Proc. Natl. Acad. Sci. USA* 88:8500–8504, 1991.

Lee, M.Y., et al., "Mechanisms of Tumor–Induced Neutrophilia: Constitutive Production of Colony–Stimulating Factors and Their Synergistic Actions," *Blood* 74:115–122, 1989.

Cassady, A.I., et al., "Isolation and characterization of the genes encoding mouse and human type–5 acid phosphatase," *Gene* 130:201–207, 1993.

Palmer, T.D., et al., "Efficient retrovirus–mediated transfer and expression of a human adenosine deaminase gene in diploid skin fibroblasts from an adenosine deaminase–deficient human," *Proc. Natl. Acad. Sci. USA* 84:1055–1059, 1987.

Oliff, A., et al., "Tumors Secreting Human TNF/Cachectin Induce Cachexia in Mice," *Cell* 50:555–563, 1987.

Purton, L.E., et al., "Normal Human Peripheral Blood Mononuclear Cells Mobilized With Granulocyte Colony–Stimulating Factor Have Increased Osteoclastogenic Potential Compared to Nonmobilized Blood," *Blood* 87:1802–1808,1996.

Matayoshi, A., et al., "Human blood–mobilized hemaotpoietic precursors differentiate into osteoclasts in the absence of stromal cells," *Proc. Natl. Acad. Sci. USA* 93:10785–10790, 1996.

Delmas, P.D., "Clinical Use of Biochemical Markers of Bone Remodeling in Osteoporosis," *Bone* 13:S17–S21, 1992.

\* cited by examiner

COMPOSITIONS FOR MEDICAL IMPLANTATION

This application is a continuation of application Ser. No. 09/063,958, filed Apr. 21, 1998, and claims the benefit of provisional application Ser. No. 60/044,033, filed Apr. 22, 1997.

This invention was made with government support under grant AR 42657 awarded by the National Institutes of Health. The government has certain rights in the invention.

FIELD OF THE INVENTION

This invention is predicated upon the discovery that tartrate-resistant acid phosphatase (TRAP) is a potent differentiating factor for osteoclasts. The invention provides, in the presently claimed embodiment, TRAP-coated bone grafts and implantable permanent orthopedic and dental prostheses.

BACKGROUND OF THE INVENTION

TRAP, also known as uteroferrin (12; see the appended Citations), purple acid phosphatase (13), or type 5 acid phosphatase (14–16), is an iron-containing, cationic glycoprotein with a molecular weight of about 35 kDa. A variety of organs including bone, spleen, lung, placenta, the pregnant pig uterus and certain leukemic cells express this enzyme (12–17). TRAP enzyme activity is detected in blood and a high enzyme level reflects active bone remodeling (18,19). In bone, the enzyme is highly expressed by multinuclear osteoclasts and mononuclear cells thought to be osteoclasts or osteoclast precursors (15). The high level of expression by osteoclasts and TRAP concentration in cytoplasmic vacuoles, extracellular channels, ruffled borders and at the cell-bone interface have implicated the enzyme in bone matrix degradation (20). The function of TRAP, however, is still unknown. A blocking antibody to porcine uteroferrin markedly inhibited both the enzyme activity and bone resorption by osteoclasts in vitro (21). Several reports point to a role for TRAP in bone remodeling. Knock-out mice lacking TRAP, generated by the homologous recombination technique, showed abnormal endochondral ossification of bones and an unusual form of mild osteopetrosis (22). A number of studies have shown that M-CSF plays a critical role in both macrophage and osteoclast maturation and function (3).

Osteoclasts, the cells that resorb bone, are essential for normal skeletal growth and remodeling. They are derived from hematopoietic progenitor/stem cells of the granulocyte/macrophage lineage, but the exact point of their divergence is controversial (1,2). While recent studies have revealed several factors involved in cell-to-cell interactions in development of osteoclast function (3,4), regulation of osteoclast progenitor differentiation and recruitment to a bone surface for resorption is still poorly understood. Better understanding of the molecular mechanisms of osteoclast differentiation and recruitment could lead to novel diagnostics and therapeutics for use in the prevention and management of osteoporosis, a common disease that results from a net imbalance between bone resorption and bone formation in the adult skeleton. This imbalance can widen when resorption accelerates after menopause associated with an increase in osteoclast numbers and resorptive activity. It is also known that certain carcinomas are prone to metastasize to bone and/or can release factors locally or systemically that promote osteolysis (bone resorption). The molecular and cellular bases of such tumor properties are not fully understood.

SUMMARY OF THE INVENTION

The invention provides, in the presently claimed embodiment, a composition or device suitable for orthopedic or dental implantation to bone, characterized by tartrate-resistant acid phosphatase (TRAP) adsorbed to a porous hydroxyapatite substratum. Such implants include autologous bone grafts, cadaveric bone allografts, hydroxyapatite-containing bone cements, prosthetic devices such as artificial joints and teeth having hydroxyapatite-coated bone attachment surfaces, and orthopedic attachment devices such as staples and plates having hydroxyapatite-coated bone contacting surfaces.

Upon implantation, the TRAP coating serves to recruit or attract osteoclast progenitor cells from the bone marrow or bloodstream to the bone implant or hydroxyapatite surface of the prosthetic or attachment device. The recruited osteoclast population etches the bone mineral or hydroxyapatite surface of the implant and thereby provides the natural signals to recruit osteoblasts to lay down new bone that will abut and integrate with the graft or prosthetic surface mimicking the natural process of bone deposition on an osteoclast resorbed bone surface. The TRAP-induced stimulation of osteoclast recruitment results in osteointegration and enhanced bonding of the graft or prosthesis to the patient's bone. This reduces recovery time from the operation and lengthens the life of implants by reducing their well-documented tendency to loosen over several years. Bone grafts also are integrated more effectively mechanically and biologically into living bone at the implant site.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

Figure 1:
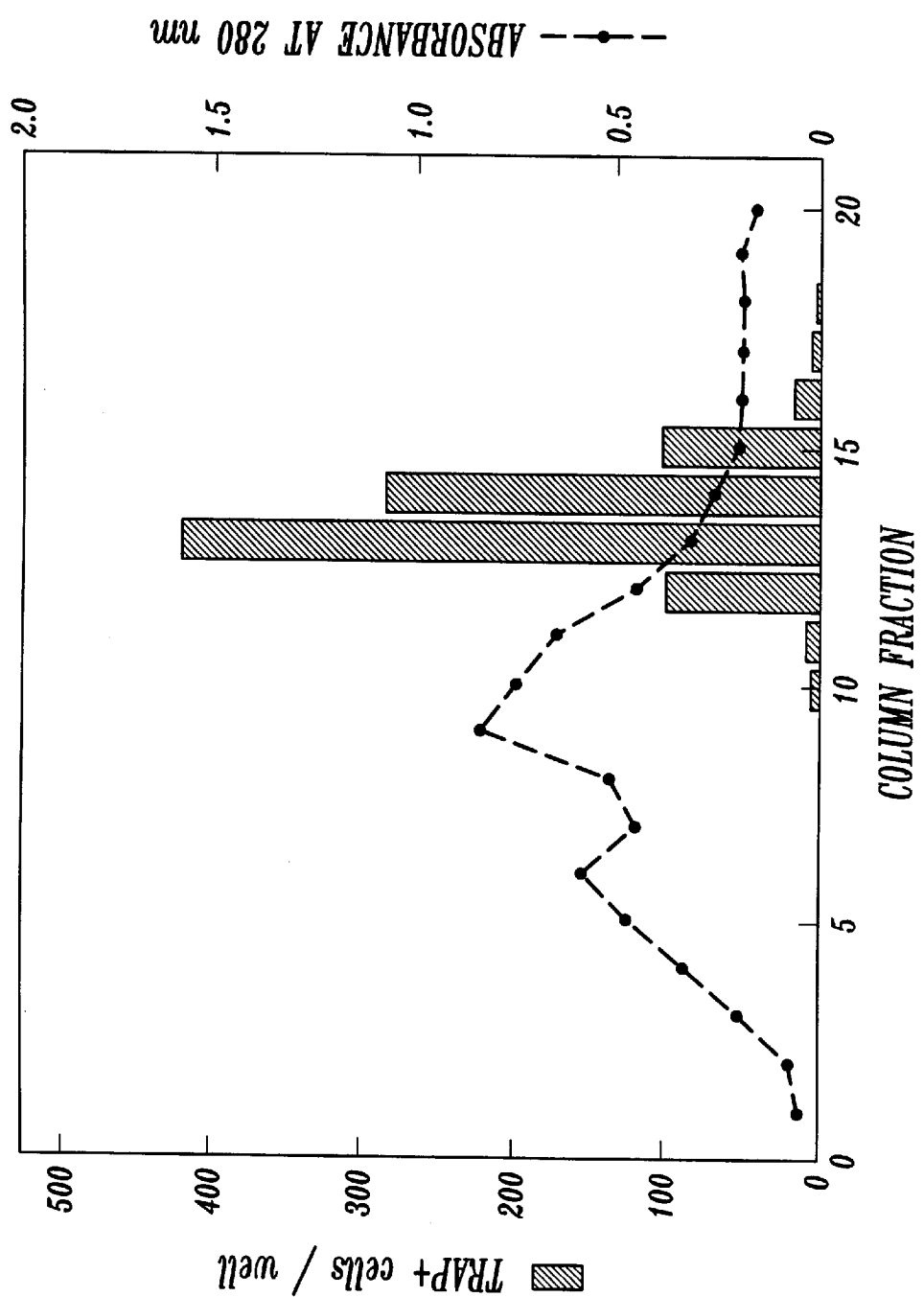
FIG. 1 shows results of protein purification of initial CESJ medium by heparin-sepharose chromatography, as described in the Examples. In this graphical data presentation, both biological activity (shaded bars) in terms of TRAP-positive cells per well, and protein content (dotted line) measured by absorbance at 280 nm, are plotted on the ordinate; and eluted column fractions are shown on the abscissa.

Here we describe the isolation and characterization of the unique factor primarily responsible for the potent osteoclast-recruiting properties of a murine mammary carcinoma cell line, CESJ. The biological activity was isolated by sequential heparin-affinity, hydroxyapatite and molecular-sieve chromatography. The molecule unexpectedly proved to be tartrate-resistant acid phosphatase (TRAP) by N-terminal sequence and enzyme activity analysis. Recombinant TRAP was prepared and shown to promote osteoclast colony formation in vitro from mouse marrow stem cells, similar to the observations for the molecule isolated from CESJ tumor cell-conditioned medium. We conclude that TRAP, perhaps through its enzyme activity as a phosphatase or generator of oxygen-derived free radicals, acts as a potent differentiating factor for osteoclasts.

We propose a role for TRAP in normal bone biology in recruiting osteoclasts to particular bone surfaces targeted for resorption and also in continuing the local recruitment of new osteoclasts to active sites of resorption by existing osteoclasts. Previous reports on an unexplained association of TRAP with osteocytes in woven bone, in the transient medullary bone of egg-laying birds and in the matrix of regions of bone and calcified cartilage destined for resorption are consistent with a role as an osteoclast recruiting agent. Medullary bone is laid down within the long bone shafts of egg-laying birds as a source of rapidly available calcium for eggshell formation (Roach, H. I. (1997) J. Bone Miner. Res. 12, 795–805). This bone is formed and rapidly resorbed in phase with the egg-laying cycle. Male birds (quail) administered estrogen will also lay down medullary bone. The matrix of medullary bone stains positively for TRAP unlike permanent bone (Yamamoto, T. and Nagai, H. (1992) J. Bone Miner. Res. 7, 1267–1273 and (1994) 9, 1153–1157). It was concluded that osteoblasts are involved in this matrix accumulation of TRAP even though the cells themselves do not stain for TRAP. These observations are consistent with the present discovery that TRAP is a potent differentiating factor for osteoclasts and with the proposed role for TRAP as a local recruiting agent for targeting osteoclasts to resorb a particular region of bone tissue. It is predicted that osteocytes and osteoblasts in certain local regions of bone can target the tissue for resorption and remodeling by expressing TRAP which becomes bound to the hydroxyapatite mineral phase of the matrix. The observed binding affinity of TRAP to hydroxyapatite might have biological significance in this proposed role of recruiting osteoclasts locally to mineralized tissue regions targeted for resorption.

The present findings reveal that TRAP has a direct role as a local factor in the recruitment of osteoclasts from hemopoietic stem cells. Thus, in normal bone physiology, the TRAP secreted by osteoclasts may act locally to recruit additional osteoclasts to differentiate from stem cells in the marrow or from circulating progenitor cells on the macrophage/osteoclast lineage. This signaling action may be mediated by the TRAP molecule acting as a ligand through a ligand/cell surface receptor mechanism or more likely by a consequence of TRAP catalytic activity, either phosphatase activity or generation of oxygen radicals or other reactive oxygen species. It was previously reported that oxygen-derived free radicals can stimulate osteoclast generation in bone cultures, but TRAP was not implicated as the source.

The present findings have practical implications for orthopedic, diagnostic, and therapeutic procedures.

Improved Bone Grafts and Prostheses

The observed binding affinity or adsorption of TRAP to hydroxyapatite has important implications for providing improved bone and dental implants. Such implants include autologous bone grafts, cadaveric bone allografts, hydroxyapatite-containing bone cements, prosthetic devices such as artificial joints and teeth having hydroxyapatite-coated bone attachment surfaces, and orthopedic attachment devices such as staples and plates having hydroxyapatite-coated bone contacting surfaces. Pursuant to the invention, enzymically active TRAP, e.g., from a recombinant source, is adsorbed to the hydroxyapatite component of the bone graft, bone cement, or device prior to implantation. In the case of autologous bone implants or banked bone tissue, the bone graft can simply be dipped in a sterile solution of TRAP in the operating theater prior to implantation. An allograft of bone implanted at a surgical site where eventual complete replacement by host bone is desired can be impregnated rather than just surface coated with TRAP. Hydroxyapatite-coated prosthetic devices can be manufactured with a predetermined penetration of adsorbed TRAP, e.g., on the order of about 10 microns, as measured for quality control by methods used histochemically to assess TRAP enzyme activity distribution in mineralized tissue sections. In any case the TRAP binds to the bone mineral (i.e., hydroxyapatite) or to the hydroxyapatite surface of the implant. Either enzymically active TRAP or a latent form that can be activated in the body by proteolysis or other means can be used.

Upon implantation, the TRAP coating serves to recruit or attract osteoclast progenitor cells from the bone marrow or bloodstream to the bone implant or hydroxyapatite surface of the prosthetic or attachment device. The recruited osteoclast population etches the bone mineral or hydroxyapatite surface of the implant and thereby provides the natural signals to recruit osteoblasts to lay down new bone that will abut and integrate with the graft or prosthetic surface mimicking the natural process of bone deposition on an osteoclast resorbed bone surface. The TRAP-induced stimulation of osteoclast recruitment results in osteointegration and enhanced bonding of the graft or prosthesis to the patient's bone. This reduces recovery time from the operation and lengthens the life of implants by reducing their well-documented tendency to loosen over several years. Bone grafts also are integrated more effectively mechanically and biologically into living bone at the implant site.

Hydroxyapatite (also known as hydroxylapatite, calcium hydroxide phosphate, calcium triphosphate, and tricalcium phosphate), $Ca_5(PO_4)_3OH$, is the major mineral component of bone. As used herein, the term "hydroxyapatite" is meant to also encompass derivative calcium phosphate compounds used in orthopedic and dental implants. A wide range of such derivative compounds have been constituted from reactions between, e.g., calcium oxide and phosphorous pentoxide. The resulting ceramics can be made in at least eight crystalline forms, with various microstructures and densities, and may contain other elements as well. (Campbell's Operative Orthopaedics, Eighth Edition, A. H. Crenshaw (Ed.), Mosby Year Book, p. 382, 1992.) (See, e.g., U.S. Pat. No. 5,171,326 entitled "Calcium phosphate ceramics for bone tissue calcification enhancement" and U.S. Pat. No. 4,097,935 entitled "Hydroxylapatite ceramic.") Porous hydroxyapatite for medical uses has also been formed by conversion of *Porites goniopora* coral exoskeleton (coralline hydroxyapatite) (Pro Osteon, Interpore International). Formulations are available for injection and in situ setting of bone fractures (e.g., SRS cancellous bone cement, Norian Corporation) to provide mechanical strength and allow for remodeling to occur with time by natural cellular mechanisms.

Porous coating's of hydroxyapatite are conventionally applied by plasmaspraying techniques to bone contacting surfaces of permanent bone prostheses. (See, e.g., U.S. Pat. No. 5,397,362 entitled "Implant prosthesis and method for producing same" and U.S. Pat. No. 5,279,831 entitled "Hydroxyapatite prosthesis coatings.") For example, in an artificial hip prosthesis, the titanium alloy stem that will be inserted into a patient's femur is coated with an approximately 50 micron thick layer of hydroxyapatite ceramic. The porous hydroxyapatite surface promotes bone growth and integration between the implant and the host, alleviating the need for acrylic bone cement, and providing enhanced mechanical force transfer. Improved functional outcome of the total joint replacement results. (For example, see U.S. Pat. No. 5,730,598, entitled "Prosthetic implants coated with hydroxylapatite and process for treating prosthetic implants plasma-sprayed with hydroxylapatite.")

In summary, this aspect of the invention provides a composition or device suitable for orthopedic or dental implantation to bone, characterized by tartrate-resistant acid phosphatase (TRAP) adsorbed to a porous hydroxyapatite substratum.

The subject compositions include bone graft compositions, wherein the hydroxyapatite substratum is selected from among autologous bone, cadaveric allograft bone, coralline hydroxyapatite, and synthetic hydroxyapatite blocks. In one embodiment, the TRAP is adsorbed throughout the porous hydroxyapatite substratum. In a preferred embodiment, the TRAP is adsorbed to only the outer surface of the porous hydroxyapatite substratum.

The subject compositions also include bone cement compositions, wherein tartrate-resistant acid phosphatase (TRAP) is adsorbed to a particulate hydroxyapatite substratum (e.g., IRC bone cement, University of London Interdisciplinary Research Centre in Biomedical Materials) which may be admixed in a self-curing acrylic polymer such as polymethylmethacrylate (PMMA). Alternatively, calcium phosphate cements which self-harden to hydroxyapatite (e.g., U.S. Pat. No. 5,525,148) can be formulated with TRAP pursuant to this invention.

The subject devices include prosthetic devices having at least one outer bone attachment surface on which tartrate-resistant acid phosphatase (TRAP) is adsorbed to a hydroxyapatite substratum. Preferably the TRAP is adsorbed to the outer approximately 10 microns of the hydroxyapatite substratum, in which case this outer layer can be spray-coated with relatively absorbable low molecular weight hydroxyapatite, prior to adsorption of the TRAP. Representative prosthetic devices for this purpose include artificial joints and artificial teeth.

The subject devices also include orthopedic attachment devices having at least one bone contacting surface on which tartrate-resistant acid phosphatase (TRAP) is adsorbed to a porous hydroxyapatite substratum. Representative attachment devices for this purpose include screws, staples, pins, bolts, and plates. For example, the bone contacting undersurface of a stainless steel plate is plasma spray-coated with hydroxyapatite, to which TRAP is subsequently adsorbed.

Diagnostics

In the management of tumors and malignancies that are potentially metastatic to bone and/or osteolytic, screening for TRAP expression by the malignant cells may be an important diagnostic tool. The present findings derived from a mouse mammary carcinoma are predictive that a subset of human breast cancers and perhaps other tumors also express TRAP. The revealed osteoclast-differentiating activity of TRAP may, therefore, explain the overt osteolytic effects of many cancers, both as primary tumors and on metastasis to bone.

One aspect of the invention accordingly involves using TRAP as a diagnostic marker for identifying osteolysis-promoting tumors at biopsy. The biopsied tissues or cells can be screened directly for TRAP expression, e.g., using available polymerase chain reaction (PCR) or in situ hybridization techniques. Direct histochemical staining methods for TRAP enzyme activity may not be reliable alone. The CESJ cell lines described here secrete abundant TRAP, but the cells do not retain and therefore stain for TRAP in the way that osteoclasts do.

Reverse transcription-polymerase chain reaction techniques, that can be applied to appropriate TRAP oligomer primers and total or poly A+ selected messenger RNA isolated from tissue samples, have been described (Veres, G., et al., 1987, Science 237:415–417; Kawasaki, E. S. 1990. Amplification of RNA. In: Innis, M. A. et al. (Eds.) PCR Protocols, A Guide to Methods and Applications. Academic Press Inc., San Diego Calif., pp. 21–27). Aberrant expression of TRAP in pathological biopsy tissue samples can also be examined by RT-PCR or by in situ hybridization techniques on fixed tissue sections with antisense TRAP probes (Hafen, E. et al., 1983. EMBO J 2:617–623; Zeller, R. and Rogers, M. 1989. In situ hybridization to cellular RNA. In: Ausubel, F. M. et al. (Eds.), Current Protocols in Molecular Biology. John Wiley and Sons, New York, pp. 14.3.1–14.3.14).

By determining that the cancer cells are expressing TRAP, the attending physician can prescribe appropriate treatment, such as a bisphosphonate to prevent osteolysis and metastatic tumor growth in bone and in combination with anticancer chemotherapy.

It is also contemplated that TRAP produced by mammary carcinomas and other tumors may have distinguishing molecular features from osteoclast TRAP, i.e., due to. novel splicing variant(s) or post-translational chemistry. This aspect of the invention accordingly provides a serum or body fluid diagnostic for potentially metastatic and/or osteolytic tumors. Conventional immunoassay techniques can be used to detect such tumor-associated TRAP molecules in a body fluid sample, using an antibody raised against the tumor-associated TRAP molecules and/or screened to detect the tumor-associated TRAP molecules but not osteoclast-associated TRAP molecules.

Therapy

The present findings also suggest new therapeutic approaches to the management of disorders of accelerated bone turnover and unbalanced bone resorption/formation.

The accelerated loss of bone after menopause in women is caused by an increased recruitment of osteoclasts and excessive bone resorption. By selectively targeting a recruitment mechanism of osteoclasts for inhibition, this process can be slowed, stopped or reversed depending on the accompanying rate of bone formation.

Thus, selective inhibitor molecules of TRAP activity can serve as novel anti-resorptive agents. One of the modes of action of bisphosphonates at the molecular level as a treatment for osteoporosis may be in inhibiting TRAP activity. TRAP cleaves inorganic pyrophosphate as a substrate, so bisphosphonates may inhibit this action and down-regulate signaling of osteoclast recruitment (for example, if generation of oxygen-derived free radicals during pyrophosphate cleavage was the local signal). Selective inhibitors of TRAP can therefore be identified, as new agents for osteoporosis treatment and prevention, for example by high-throughput screening using recombinant TRAP to identify candidate molecules. Microwell assays for TRAP phosphatase or pyrophosphatase activity can be based for example on colored chromogen generation (e.g., p-nitrophenyl phosphate cleavage) and used to screen for selective inhibitors. Alternatively, oxygen radical generating activity of TRAP can be screened using luminol as the substrate in the presence of hydrogen peroxide and measuring chemiluminescence production. Histological methods at the light microscope level can also be used to screen for agents that inhibit TRAP enzyme activity (Fukushima, O., Bekker, P. J. and Gay, C. V. (1991) Amer. J. Anat. 191:228–236). Such approaches may be adapted to recombinant TRAP spotted or otherwise adsorbed on thin layers of hydroxyapatite for screening of activity and inhibition microscopically. In particular, small molecule inhibitors that do not become incorporated into the fabric of bone mineral can be identified as desirable alternatives to bisphosphonates. Such compounds can be sought by standard approaches in medicinal chemistry with reference to knowledge of the properties of known inhibitors of TRAP, which include molybdate, tungstate, arsenate, fluoride, phosphate and dithionite ions (Allen et al. (1989) J. Bone Miner. Res. 4:47–55). Other candidates include vitamin E analogs and other compounds that are known to inhibit oxygen-derived radical generation or scavenge reactive oxygen species. Compounds that have minimal toxicity yet selectivity for the TRAP activity that promotes osteoclast differentiation are particularly desirable. A secondary screen seeking efficacy in blocking osteoclast recruitment can be based on microwell cultures of bone marrow or spleen cells or other sources of osteoclast progenitors, and TRAP (e.g., a recombinant preparation) adsorbed on a suitable solid-phase surface (e.g., thin layer of hydroxyapatite coated on an inert substratum or particles of bone or. dentin). Inhibition of the attachment of differentiated osteoclasts as observed microscopically can be used as the outcome measure. Families of compounds can be rapidly screened in this way for a functional outcome in vitro. Compounds that are adsorbed on the bone mineral surface, for example through an incorporated bisphosphonate group that will not directly block osteoclast resorbing activity, but down-regulate osteoclast recruitment to the surface, are desirable. Such TRAP inhibitory agents when administered to patients turn down the osteoclast-recruiting activity of TRAP, leading to a beneficial effect in bone mass.

As noted above, TRAP enzyme activity is inhibited by molybdate, tungstate, arsenate, fluoride, phosphate and dithionite. The potent bone-forming properties of fluoride have not been fully explained. Given the present findings, local inhibition of osteoclast recruitment by inhibition of TRAP activity is one potential contributing mechanism, thereby imbalancing the coupled resorption and formation activities at remodeling sites in favor of formation. The mechanism of action of the various bisphosphonates in blocking osteoclastic resorption is not fully understood. Blocking of terminal differentiation of osteoclast progenitors is one observed action. Though bisphosphonates are considered to be relatively poor inhibitors of TRAP activity (Allen et al., (1989) J. Bone Miner. Res. 4:47–55), no extensive studies appear to have been carried out comparing the inhibitory action of the various bisphosphonates now approved or undergoing trial for clinical use. If the persistent gain in bone produced clinically by alendronate and other bisphosphonates in part reflects an inhibition of the TRAP activity responsible for recruiting osteoclast teams for resorption, yet permitting formation to exceed resorption at remodeling sites, then an additional therapeutic strategy is contemplated. Agents that stimulate or emulate TRAP activity could be given to activate resorption followed by a bisphosphonate to block resorption and build bone at the activation sites. Such cyclic, combination therapy could be used as a treatment for maximizing the therapeutic benefits of bisphosphonate therapy. Compounds having desired therapeutic properties could be screened using recombinant TRAP and appropriate culture and assay systems in vitro.

In this embodiment, TRAP or a TRAP emulator molecule (e.g., a binuclear iron-containing small molecule) is administered as an agent to recruit osteoclast activity followed by administration of an anti-resorptive agent to promote a net imbalance in remodeling in favor of enhanced bone formation. Here the goal is to activate as many bone surfaces as possible by adsorbing TRAP to recruit osteoclast attachment to them, then shut down the process after a short period (several days) by an inhibitor of osteoclasts before a significant amount of bone is lost. Maximal recruitment of osteoblasts to build new bone will then occur. Representative anti-resorptive agents include bisphosphonates, estrogen and estrogen mimics, and calcitonins. Such a strategy has been proposed and referred to as "ADFR" (for Activate, Depress, Free and Repeat), but using other agents to recruit the resorption phase of the bone remodeling cycle (Frost, H. M., Clin. Orthop. 143:227–244, 1979; Frost, H. M., Calcif. Tissue Intern. 36:349–353, 1984). The principle is to cycle the therapeutic regimen and so maximize the growth of new bone. In this way, bone mass may be built back, for example, to treat advanced osteopenia or prevent osteoporosis later in life for individuals (for example, post-menopausal women) who already show low bone mass or other risk factors for osteoporosis. The advantage of TRAP in this approach is high specificity in recruiting osteoclasts.

Recombinant TRAP might be administered to do this, but smaller molecules that emulate TRAP osteoclast-recruiting activity (e.g., oxygen-derived free radical generation) can also be designed to attach to mineral surfaces of bone (e.g., using a bisphosphonate that has weak or no osteoclast-inhibiting activity linked covalently to an oxygen radical generating organic group).

A further embodiment is the measurement of type I collagen metabolites, preferably urinary NTx by the OSTEOMARK® Assay (Ostex International, Inc., Seattle, Wash.), to monitor the increase in bone resorption and hence time the administration of the anti-resorptive agent for maximum benefit. The NTx analyte is also used to determine that the bone resorption has been returned to the normal (baseline) range at the end of the therapeutic cycle. A suitable animal model for investigating this therapeutic strategy is the guinea pig. Recombinant TRAP is administered by injection, implanted osmotic pump, TRAP gene transfer, or other method. The NTx analyte can be measured in guinea pigs because the monoclonal antibody supplied with the OSTEOMARK® Assay cross-reacts equally with human and guinea pig NTx. The dosages of TRAP and anti-resorptive agent (e.g., alendronate sodium or other bisphosphonate) can be titered and defined based on baseline NTx, TRAP stimulated NTx, and suppressed NTx levels. The benefits in terms of increased bone mass can be monitored by dual x-ray absorptiometry (DEXA) or other bone densitometric techniques.

EXAMPLES

Materials and Methods

Tumor-cell conditioned medium: CESJ, Bc66, or Bc-TRAP cells were cultured in serum-free medium. Culture supernatant was concentrated 500-fold for CESJ, and 100-fold for Bc66 or Bc-TRAP cell medium.

Bone marrow colony assays: Bone marrow cells were obtained from C57Black 6 mice. Mice were housed in the vivarium of University of Washington, and the animal care and experiments were conducted in accordance with the institutional guidelines. Bone marrow cells were cultured at $10^5$ cells per ml in culture medium containing 20% (v/v) fetal calf serum, 0.3% agar or 0.25% agarose (agarose was used in experiments where colonies were harvested for mRNA isolation), and various concentrations of test samples. Cell cultures were incubated for 14 days at 37° C. in a humidified atmosphere with 5% $CO_2$ and were stained for TRAP activity after fixation as described (7). Stained slides were evaluated under the microscope for TRAP positive single cells, clusters (>8 cells, <50 cells) or colonies (>50 cells) as previously defined (7).

Enrichment of bone marrow progenitor cells: Adherent cells were depleted from mouse whole bone marrow cells by passing through Sephadex G10 columns, and the cells with low density were selected using a Percoll density gradient method. The cells expressing specific lineage markers were eliminated by monoclonal antibodies specific for murine B cells (B220), granulocytes (Gr-1), macrophages (Mac-1) and erythrocytes (YW25.12.7) on MACS (Miltenyi Biotec)using magnetic beads conjugated with goat anti-rat IgG, and cells negative for above lineage markers (Lin-) were used as the target cell population of the isolated protein. Colony forming hematopoietic progenitors and osteoclast progenitors have been shown to be enriched in the Lin- cell population (Muguruma and Lee, Blood, 91:1272–1279: 1998).

Preliminary Observations

The bones of mice bearing CE mammary carcinoma exhibit markedly increased numbers of osteoclasts with evidence of excessive bone resorption (5).

Serum-free culture supernatant of cloned cell lines (CESJ) of this tumor had a unique ability to induce colonies of cells exhibiting intense TRAP activity in mouse bone marrow cells cultured in semi-solid medium. The activity directly affected progenitors rather than being mediated through or in conjunction with accessory cells since clonogenic progenitor cells isolated from marrow also responded to CESJ medium and formed TRAP-positive colonies (8). Furthermore, TRAP-positive colonies induced from isolated progenitors by CESJ medium expressed the osteoclast markers: vitronectin receptor $\alpha_v\beta 3$, $pp^{c\text{-}src}$ and the calcitonin receptor, and formed resorption pits during further cultivation under appropriate culture conditions (8).

In contrast, the culture supernatant of another mammary carcinoma cell line, Bc66 (6,7), did not possess such osteoclast inducing activity despite containing macrophage colony stimulating factor (M-CSF), and the parent tumor was non-osteolytic in mice. Furthermore, using recombinant mouse M-CSF to induce macrophage colonies under similar assay conditions, the colonies were always negative for TRAP staining even in the presence of $1,25(OH)_2D_3$ ($10^{-8}$M) and hydrocortisone ($10^{-6}$M) (data not shown).

In earlier work, one active component was purified from CESJ medium and shown to be an osteoclast colony stimulating factor (O-CSF) (6). During further analysis of the osteoclast stimulating activity of CESJ medium, it became apparent that another potent factor was present in the medium that induced TRAP-positive cells to differentiate from bone marrow cells in culture.

Isolation of Osteoclast Differentiating Factor (ODF)

Over 100 L of serum-free conditioned medium from cultures of a CESJ clone (8) was used to isolate and characterize the factor. Conditioned medium of CESJ cells was fractionated by sequential column chromatography on heparin-sepharose, hydroxyapatite and molecular-sieve HPLC (Toso Haas TSK gel, G3000 SW). Osteoclast-inducing activity was monitored by an assay in which mouse bone marrow cells were cultured for 14 days in semi-solid agar (6,7). Colonies, clusters or single cells derived from osteoclast progenitors were detected by their bright red appearance on staining for TRAP activity.

FIG. 1 presents results of protein purification of the initial medium by Heparin-Sepharose column chromatography. Heparin sepharose CL-6B (Pharmacia Biotech) packed in an Econo-Pac column (Bio-Rad; 1.5×4 cm) was equilibrated with 20 mM Tris-HCl containing 0.1M NaCl, pH 7.2. Aliquots of 40 ml of 100×concentrated CESJ medium were equilibrated into the above buffer and applied to the column for each run. About 95% of the total protein passed through the column as estimated by UV absorbance at 280 nm. After washing the column with the same buffer overnight, proteins bound to the column were eluted by a linear 0.1–0.7M of NaCl gradient in 20mM Tris-HCl (pH 7.2) at a flow rate of 0.7 ml/min at 22° C. A portion of each collected fraction was tested for ODF activity in the marrow culture assay after re-equilibrating into 20 mM Tris-HCl buffer (pH 7.2) and filtering (0.22 $\mu$M, Millipore).

FIG. 1 shows that, on heparin column chromatography, ODF activity was consistently recovered in the bound fraction eluted at about 0.47 M NaCl. In contrast, M-CSF and granulocyte-CSF (G-CSF), both of which were present in the CESJ medium (9) were not bound to heparin. The previously described O-CSF activity (6) was also not bound. The heparin-bound ODF activity induced intensely TRAP-positive single cells or clusters of 4 to 8 cells in the marrow culture assay, but TRAP-positive colonies of more than 50 cells as induced by whole CESJ medium were rather rare. Combining the heparin-bound active fraction and the unbound pool restored the original TRAP-positive colony stimulating activity of the CESJ medium.

Figure 2:
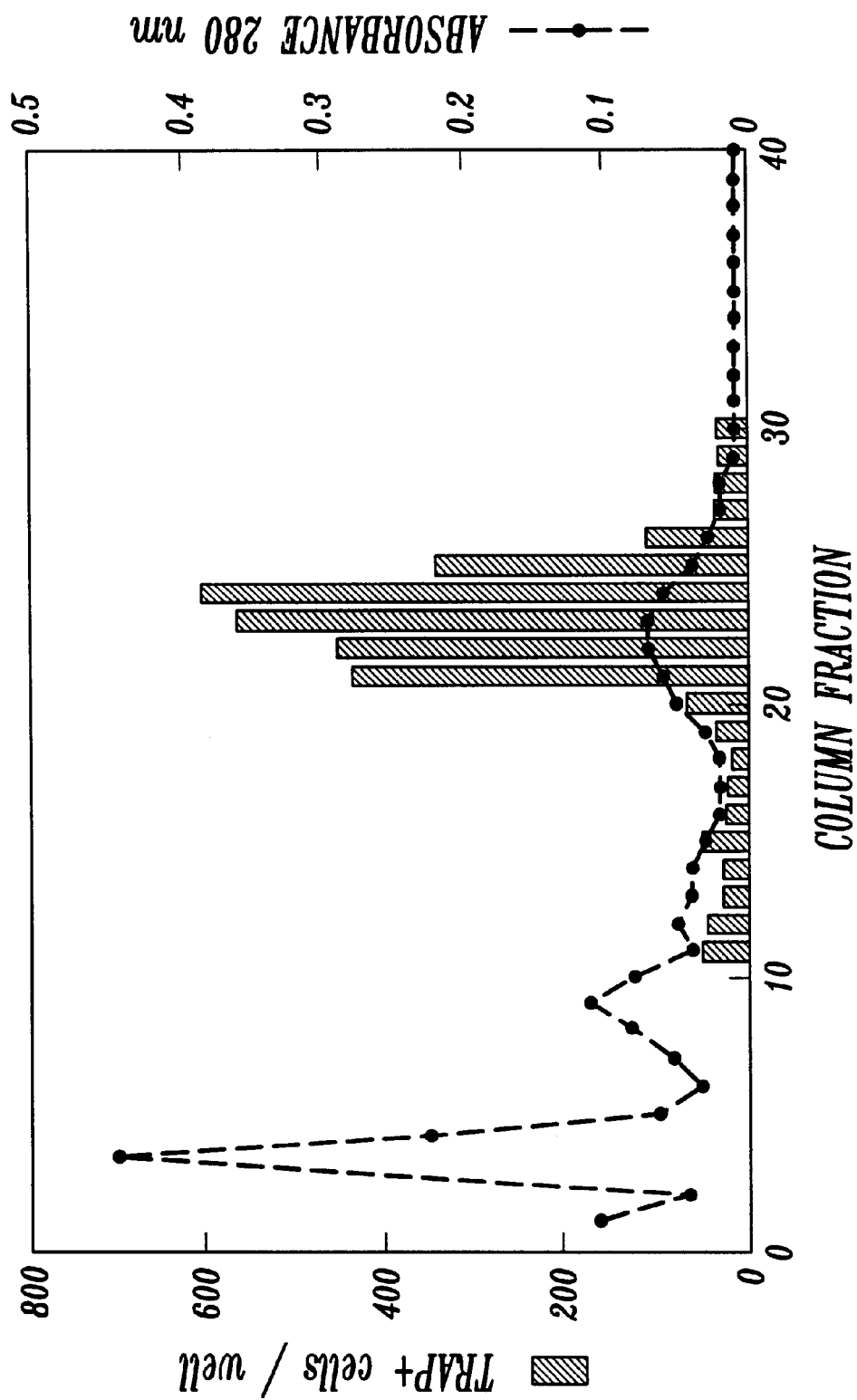
FIG. 2 shows further purification of TRAP-positive activity on a hydroxyapatite column. The data are plotted on the ordinate and abscissa here as in FIG. 1.

The ODF activity from the heparin column was bound to the hydroxyapatite column and eluted at about 170 mM phosphate (FIG. 2): The fractions containing ODF activity from heparin-sepharose were pooled, concentrated and equilibrated by centrifugal filtration through a Centricon membrane into 10 mM sodium phosphate, pH 7.0, and applied to a hydroxyapatite column (Econo-Pac, CHT-11 Cartridge, Bio-Rad). The column was washed with 10 mM sodium phosphate, pH 7.0. Bound proteins were eluted with a linear 10 to 300 mM Na phosphate gradient (pH 7.0). Portions of each fraction were assayed for ODF activity and analyzed for proteins by 14% SDS-PAGE. Material in the fraction which eluted at about 170 mM phosphate induced TRAP positive mononuclear cells in the bone marrow culture assays, but when combined with recombinant murine M-CSF it induced TRAP-positive colony formation.

Figure 3A:
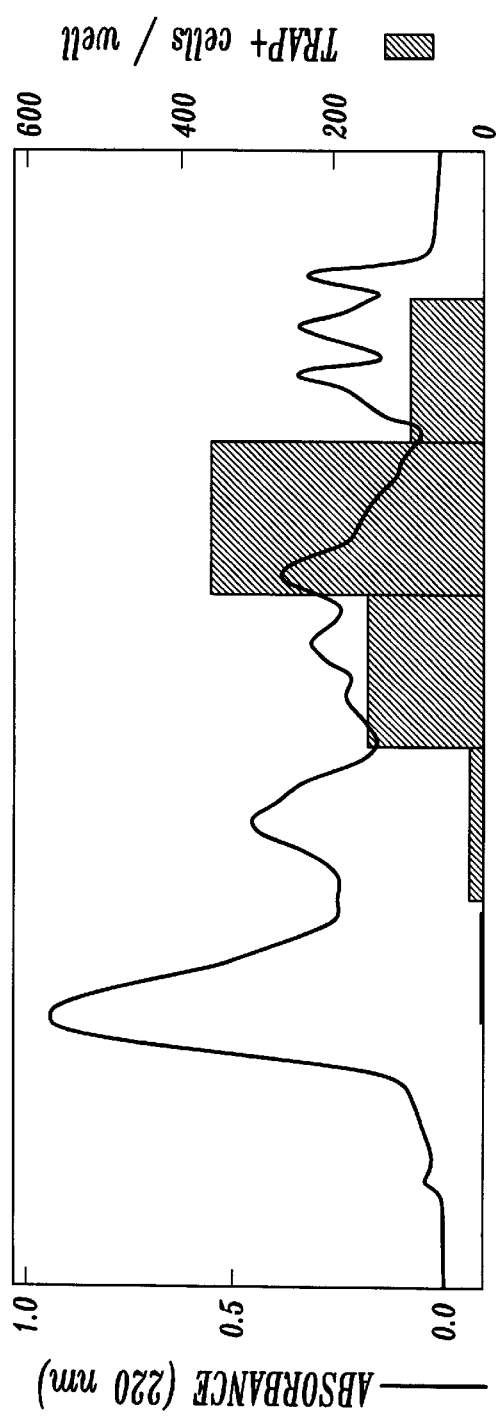
FIG. 3 shows final isolation of TRAP by size-exclusion column HPLC. Here, both biological activity (shaded bars) in terms of TRAP-positive cells per well, and protein content (solid trace) measured by absorbance at 220 nm, are plotted on ordinate of the upper graph (FIG. 3A), and TRAP enzyme activity, measured by p-nitro phenyl phosphate cleavage, is plotted on the ordinate of the lower graph (FIG. 3B) in terms of mUnits of TRAP/ml (dotted line); elution volume (ml) is shown on the common abscissa.
Figure 3B:
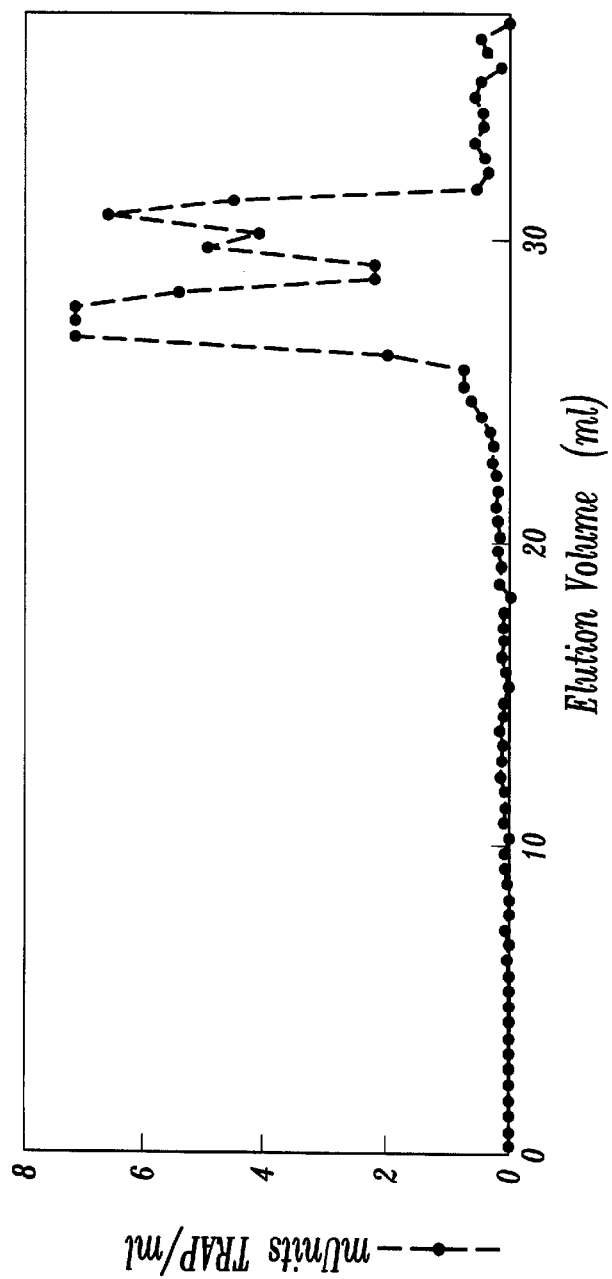

Active fractions from several hydroxyapatite column runs were combined and run on size-exclusion column HPLC (SEC-HPLC) in 0.1M phosphate buffer (pH 6.8) containing 30% (v/v) acetonitrile (FIG. 3). By SDS-PAGE the ODF activity appeared to coincide with the elution position of a 35 kDa protein.

In detail, the active fractions from hydroxyapatite column chromatography were pooled, concentrated by Centricon ultrafiltration, adjusted to 30% (v/v) acetonitrile and the sample was fractionated by size exclusion HPLC (two Toso-Haas G3000SW, 7.5 mm×60 cm in series) equilibrated with 0.01M Na phosphate buffer, pH 6.8, containing 30%

(v/v) acetonitrile. The eluent was monitored for protein absorbance at 220 nm. Fractions (0.5 ml) were collected into tubes containing 0.02% (w/v) CHAPS (Calbiochem). Samples pooled every 10 fractions were tested for TRAP-positive cell stimulating activity.

Identification of the Osteoclast Differentiating Factor

Pooled fractions corresponding to the regions of biological activity from another aliquot of the hydroxyapatite pool run identically on SEC-HPLC were dried for amino-terminal sequence analysis (Porton 2090E equipped with on-line HPLC analysis of phenylthiohydantoin amino acid derivatives). The only N-terminal sequence evident in fractions between 24–32 ml of elution volume was APTPTLR-FVAV which corresponds to the N-terminus of mouse TRAP, minus its signal peptide (23). In this region of column eluent, and in earlier fractions where biological activity was also detected, the 35 kDa protein band was evident. The size and sequence were consistent with the TRAP protein (band 5 TRAP isoenzyme;

EC 3.1.3.2). No other match or near homology to another gene was found by genomic or protein data-base search.

TRAP activity was, therefore, measured in a 96-well microtiter plate. Assay for TRAP enzyme activity using p-nitrophenol phosphate as substrate in the presence of tartrate confirmed the presence of active enzyme in the various column fractions and in the original CESJ culture medium. A 100 $\mu$l sample (20 $\mu$l column fraction +80 $\mu$l $H_2O$) was added to 100 $\mu$l 0.2M Na acetate, 40 mM Na tartrate, 16 mM p-nitrophenyl phosphate, 5 mM dithiothreitol, pH 5.7. After incubating at 37° C. for 1 hr, 20 $\mu$l 0.5M Na OH was added and absorbance at 405 nm was measured. Column fractions from an SEC-HPLC run were analyzed on SDS-PAGE, staining with silver. Bc66 medium, in contrast, showed no enzyme activity. The activity was shown to be inhibited by molybdate, a known inhibitor of TRAP.

Confirming Experiments

To confirm that TRAP was responsible for the ODF activity, the recombinant enzyme was expressed in two cell lines, Bc66 and Chinese hamster ovary (CHO) cells. Bc66 cells were transduced by a retroviral vector to express rat TRAP (10).

Conditioned medium of transduced cells (BcTRAP) demonstrated abundant TRAP enzyme activity and stimulated intensely TRAP-positive colonies. In contrast, medium of control Bc66 cells stimulated only TRAP-negative colonies. Bc66 cells are known to produce M-CSF. Therefore, CHO cells, which do not produce M-CSF, were transfected with the vector containing rat TRAP gene (11). The conditioned medium of transfected CHO cells (CHO-TRAP) stimulated TRAP-positive colonies while control CHO cell medium did not show any TRAP inducing or colony stimulating ability. While M-CSF alone stimulated only TRAP-negative colonies, M-CSF and TRAP together stimulated large TRAP-positive colonies suggesting a synergism of TRAP and M-CSF in cell proliferation. This discovery suggests that both TRAP and M-CSF might work in conjunction to drive the lineage to osteoclasts with TRAP inducing differentiation and M-CSF proliferation.

To rule out the possibility that the exogenous TRAP might be directly responsible for the observed TRAP-positive staining of the cells in the marrow cultures, TRAP mRNA expression was assessed. A fraction of mouse marrow cells selected on the basis of being lineage-marker negative (Lin-), and shown to be enriched in osteoclast progenitors (8) was used. Isolated Lin- cells were cultured in semi-solid medium in the presence of concentrated conditioned medium from CHO-TRAP or CHO control cells. MnRNA isolated at 7 days and 14 days showed the expression of endogenous TRAP in the TRAP-positive colonies.

The timing of TRAP addition to bone marrow progenitor assays was examined by overlaying the purified TRAP onto agar cultures containing Lin- cells and M-CSF at various days of the culture and evaluating the colonies formed 14 days after the overlays. TRAP-positive colony formation was observed only when purified TRAP was added during the first 48 hours of culture. Addition of TRAP later in the culture resulted in the growth of macrophage colonies. Taken together, these experimental data strongly suggest a critical role for TRAP in osteoclast differentiation. This enzyme seems to act on immature progenitors of the monocyte-macrophage pathway and induce osteoclast differentiation prior to their commitment to macrophages.

Transduced BcTRAP cells and Bc66 cells were also subcutaneously transplanted into Balb/c nude mice to assess the in vivo effects of a TRAP-producing tumor. Microscopic examination of various tissues revealed notable changes only in bone. Morphometric analyses of bone from the tumor-bearing mice revealed an increased osteoclastic activity and thinning of long-bone cortical walls in mice transplanted with BcTRAP when compared with mice transplanted with normal Bc66 cells. The results essentially reproduced the original findings with CE tumor-bearing mice. TRAP therefore appears to be the critical factor responsible for the unique osteoclast-inducing properties of the CE mammary tumor cells.

Confirmation of Implant Efficacy In Vivo Mouse or human TRAP can be expressed by recombinant means, for example in Sf9 insect cells from a recombinant baculovirus vector construct (Hayman, A. R. and Cox, T. M. (1994), J. Biol. Chem. 269:1294–1300; Ek-Rylander, B. et al. (1997) Biochem. J. 321:305–311). Enzymatically active TRAP containing two iron atoms per molecule can be purified from the culture medium in mg/L quantities. Both phosphatase and oxygen radical generating activities can be demonstrated respectively by cleavage of p-nitro phenylphosphate or peroxidation of luminol and chemiluminescence release.

The ability of TRAP (recombinant or prepared from natural sources such as CESJ-conditioned medium) to promote osteoclast recruitment to implant surfaces can be assessed in animals in vivo. In one approach, a purified TRAP preparation shown to be enzymatically active is dissolved in neutral buffer at low ionic strength. Solid-phase preparations of hydroxyapatite (or other calcium salt solid phases, e.g., thin layers coated on biologically inert membranes or free-standing blocks) are immersed in the TRAP solution to bind or adsorb TRAP molecules to the surface layer of hydroxyapatite. By cutting and staining sections for TRAP activity histochemically, using azo dye or lead salt methods (Yamamoto, T. and Nagai, H. (1992) J. Bone Miner. Res. 7:1267–1273), the length of time needed to adsorb a particular thickness and activity of TRAP can be controlled. Whole preparations can also be stained using a substrate for TRAP according to prior histological techniques. Appropriately TRAP-coated hydroxyapatite preparations are then implanted surgically into experimental animals either subcutaneously or intramuscularly. In one example, murine TRAP is used in mice as the experimental animal. A hydroxyapatite vehicle (hydroxyapatite-coated membrane or solid block lacking TRAP) is implanted at an adjacent but separate site in the same animal to serve as a control. To augment the number of osteoclast progenitors in the circulation, experimental animals can be primed with factors such as G-CSF that enhance stem cell mobilization from the bone marrow to the bloodstream (Purton, L. E., et al., Blood 87:1802–1808,1996; Matayoshi, A., et al., Proc Natl Acad Sci USA 93:10785–10790, 1996).

Alternatively, mineralized bone or dentin particles or slices can be coated with TRAP and implanted similarly, again using uncoated material as the control for comparison.

After 7–14 days, animals are sacrificed and the retrieved implants are examined histologically for osteoclast attachment using established methods. The osteoclast recruiting activity of TRAP-coated hydroxyapatite surfaces can be thus demonstrated. In a variation of this approach, discrete regions of the solid hydroxyapatite surface can be selectively treated with TRAP and after retrieval from the animals, histological examination can confirm an attraction of osteoclasts preferentially to the TRAP-coated surfaces.

The ability of TRAP to promote osteointegration into or onto metal (or ceramic or other fabricated) implant surfaces as used in joint replacements or dental prosthetic devices seated into bone can also be investigated in animals. Preparations of hydroxyapatite-coated titanium alloys (rods, plates or other suitably sized fabrications) are coated with TRAP and implanted surgically into or onto bone surfaces in experimental animals. Here, the objective is a longer term evaluation of the osteointegration of the bone bed against a plain surface or into a porous surface of a metal implant. Both smooth and porous-coated surface designs are used in metal prostheses, for example the femoral stem component used in total hip replacements. Representative porous metal coatings for ingrowth of bone include cobalt-chrome powder or beads (Porocoat surface, DePuy; PCA, Howmedica) and the diffusion bonding of titanium wire mesh (Zimmer). Such porous metal surfaces are preferably first coated with hydroxyapatite by plasma-spraying techniques, before coating with TRAP. Osteointegration is judged in individual animals at time intervals of 1–12 months after surgery by x-ray imaging to evaluate degree of radiolucency, and hence gap between metal and bone, and by retrieval, sectioning and microscopy of the metal/bone interface of the implant. Such methods are commonly in use by implant manufacturers to evaluate new materials, fabrications and other aspects of prosthetic design. In this way, the advantages of TRAP-coated surfaces for promoting osteointegration is established and the coating protocol optimized for different clinical applications.

It is further contemplated that other biological materials can be included with TRAP in the mineral-phase substratum to promote bone attachment. Representative biological materials for this purpose include cytokines or other signaling molecules and collagen, the latter to enhance mechanical coupling of the new bone matrix to the implanted composition or device.

While the invention has been described in conjunction with preferred embodiments, one of ordinary skill after reading the foregoing specification will be able to effect various changes, substitutions of equivalents, and alterations to the subject matter set forth herein. Hence, the invention can be practiced in ways other than those specifically described herein. It is therefore intended that the protection granted by Letters Patent hereon be limited only by the appended claims and equivalents thereof Citations 1. Roodman, G. D.: Advances in bone biology: The osteoclast. Endocrine Reviews 17:308–332, 1996.
2. Suda, T., et al., Bone 17(2S):87S–91S, 1995.
3. Suda, T., et al., Endocrine Reviews 13:66–80 1992.
4. Yasuda, H., et al., Proc. Natl. Acad. Sci. USA 95:3597–3602, 1998.
5. Lee, M. Y., and Baylink, D. J., Proc. Soc. Exp. Biol. Med. 172:424–429, 1983.
6. Lee, M. Y., et al., Proc. Natl. Acad. Sci. USA 88:8500–8504, 1991.
7. Lee, M. Y., et al., Blood 80:1710–1716, 1992.
8. Muguruma, Y., and Lee, M. Y., Blood 91:1272–1279, 1998.
9. Lee, M. Y., et al., Blood 74:115–122, 1989.
10. Palmer, T. D., et al., Proc. Natl. Acad. Sci. USA 84:1055–1059, 1987.
11. Oliff, A., et al., Cell 50:555–563, 1987.
12. Ling, P., and Roberts, R. M., J. Biol. Chem. 268:6896–6902, 1993.
13. Hayman, A. R., and Cox, T. M., J. Biol. Chem. 269:1294–1300, 1994.
14. Ketcham, C. M., et al., J. Biol. Chem. 264:557–563, 1989.
15. Ek-Rylander, B., et al., J. Biol. Chem. 266:24684–24689, 1991.
16. Ek-Rylander, B., et al., Biochem. J. 321:305–311, 1997.
17. Yam, L. T., et al., N. Engl. J. Med. 284:357–360, 1971.
18. Lau, K. H., et al., Clin. Chem. 33:458–462, 1987.
19. Chamberlain, P., et al., Clin. Chem. 41:1495–1499, 1995.
20. Reinholt, F., et al., J. Bone Miner. Res. 5:1055–1061, 1990.
21. Zaidi, M., et al., Biochem. Biophys. Res. Commun. 159:68–71, 1989.
22. Hayman, A. R., et al., Development 122:3151–3162, 1996.
23. Cassady, A. I., et al., Gene 130:201–207, 1993.

The entire disclosures of the prior publications and patents cited in this patent application are incorporated by reference herein.

The embodiments of the invention in which an exclusive property or privilege is claimed are defined as follows:

1. A composition suitable for medical implantation comprising tartrate-resistant acid phosphatase (TRAP) adsorbed to a porous hydroxyapatite substratum.

2. A bone graft composition according to claim 1.

3. The bone graft composition of claim 2, wherein the hydroxyapatite substratum is selected from among autologous bone, cadaveric allograft bone, and coralline hydroxyapatite.

4. The bone graft composition of claim 2, wherein the TRAP is adsorbed throughout the porous hydroxyapatite substratum.

5. The bone graft composition of claim 2, wherein the TRAP is adsorbed to only the outer surface of the porous hydroxyapatite substratum.

6. A bone cement composition according to claim 1, comprising tartrate-resistant acid phosphatase (TRAP) adsorbed to a particulate hydroxyapatite substratum admixed in a curable acrylic polymer.

7. An orthopedic attachment device having a bone contacting surface comprising tartrate-resistant acid phosphatase (TRAP) adsorbed to a porous hydroxyapatite substratum.

8. The orthopedic attachment device of claim 7, selected from among a screw, a staple, a pin, a bolt, and a plate.

* * * * *